(12) United States Patent
Patel et al.

(10) Patent No.: US 7,736,665 B2
(45) Date of Patent: Jun. 15, 2010

(54) IMPLANTABLE POLYMERIC DEVICE FOR SUSTAINED RELEASE OF BUPRENORPHINE

(75) Inventors: Rajesh A. Patel, Redwood City, CA (US); Louis R. Bucalo, Miami Beach, FL (US)

(73) Assignee: Titan Pharmaceuticals, Inc., South San Francisco, CA (US)

( * ) Notice: Subject to any disclaimer, the term of this patent is extended or adjusted under 35 U.S.C. 154(b) by 373 days.

(21) Appl. No.: 10/453,377

(22) Filed: Jun. 2, 2003

(65) Prior Publication Data

US 2004/0033250 A1 Feb. 19, 2004

Related U.S. Application Data (60) Provisional application No. 60/384,733, filed on May 31, 2002.

(51) Int. Cl.
*A61F 2/00* (2006.01)
(52) U.S. Cl. .................. 424/423; 424/422; 514/772; 514/772.3; 514/772.4
(58) Field of Classification Search .................. None
See application file for complete search history.

(56) References Cited

U.S. PATENT DOCUMENTS

| | | | | |
|---|---|---|---|---|
| 3,689,634 | A | * | 9/1972 | Kliment et al. ............. 424/475 |
| 3,717,639 | A | | 2/1973 | Neumeyer |
| 3,814,768 | A | | 6/1974 | Fishman |
| 4,069,307 | A | | 1/1978 | Higuchi et al. |
| 4,148,871 | A | | 4/1979 | Pitt et al. |
| 4,351,337 | A | | 9/1982 | Sidman |
| 4,450,150 | A | | 5/1984 | Sidman |
| 4,464,378 | A | | 8/1984 | Hussain |
| 4,535,157 | A | | 8/1985 | Meltzer et al. |
| 4,543,256 | A | | 9/1985 | Neumeyer |
| 4,582,835 | A | | 4/1986 | Lewis et al. |
| 4,599,342 | A | | 7/1986 | LaHann |
| 4,622,219 | A | | 11/1986 | Haynes |
| 4,661,492 | A | | 4/1987 | Lewis et al. |
| 4,670,014 | A | | 6/1987 | Huc et al. |
| 4,678,809 | A | | 7/1987 | Phillips |
| 4,692,451 | A | | 9/1987 | Dodman et al. |
| 4,725,442 | A | | 2/1988 | Haynes |

(Continued)

FOREIGN PATENT DOCUMENTS

EP 0 069 600 1/1983

(Continued)

OTHER PUBLICATIONS

PDR Drug Information for Buprenorphine Hydrochloride, downloaded from the world wide web on Jul. 20, 2006.*

(Continued)

*Primary Examiner*—Eric E. Silverman
(74) *Attorney, Agent, or Firm*—Morrison & Foerster LLP (57) ABSTRACT

The present invention provides compositions, methods, and kits for treatment of opiate addiction and pain. The invention provides a biocompatible nonerodible polymeric device which releases buprenorphine continuously with generally linear release kinetics for extended periods of time. Buprenorphine is released through pores that open to the surface of the polymeric matrix in which it is encapsulated. The device may be administered subcutaneously to an individual in need of continuous treatment with buprenorphine.

9 Claims, 4 Drawing Sheets

U.S. PATENT DOCUMENTS

| | | | |
|---|---|---|---|
| 4,818,542 A | | 4/1989 | DeLuca et al. |
| 4,844,903 A | * | 7/1989 | Seth .......................... 424/448 |
| 4,861,627 A | | 8/1989 | Mathiowitz et al. |
| 4,882,335 A | | 11/1989 | Sinclair |
| 4,883,666 A | | 11/1989 | Sabel et al. |
| 4,897,268 A | | 1/1990 | Tice et al. |
| 4,898,733 A | | 2/1990 | DePrince et al. |
| 4,935,428 A | | 6/1990 | Lewis |
| 4,957,119 A | | 9/1990 | de Nijs |
| 4,962,091 A | | 10/1990 | Eppstein et al. |
| 4,983,586 A | | 1/1991 | Bodor |
| 4,994,281 A | | 2/1991 | Muranishi et al. |
| 5,024,998 A | | 6/1991 | Bodor |
| 5,069,909 A | | 12/1991 | Sharma et al. |
| 5,075,341 A | | 12/1991 | Mendelson et al. |
| 5,086,058 A | | 2/1992 | Sinclair et al. |
| 5,114,718 A | | 5/1992 | Damani |
| 5,114,719 A | | 5/1992 | Sabel et al. |
| 5,128,145 A | | 7/1992 | Edgren et al. |
| 5,149,538 A | * | 9/1992 | Granger et al. .............. 424/449 |
| 5,156,844 A | | 10/1992 | Aebischer et al. |
| 5,211,951 A | | 5/1993 | Sparer et al. |
| 5,219,858 A | | 6/1993 | Parnell |
| 5,236,714 A | * | 8/1993 | Lee et al. .................... 424/449 |
| 5,238,933 A | * | 8/1993 | Catz et al. ................. 514/236.2 |
| 5,240,711 A | | 8/1993 | Hille et al. |
| 5,298,017 A | * | 3/1994 | Theeuwes et al. ............. 604/20 |
| 5,478,577 A | | 12/1995 | Sackler et al. |
| 5,486,362 A | | 1/1996 | Kitchell et al. |
| 5,503,844 A | * | 4/1996 | Kwiatek et al. ............. 424/449 |
| 5,562,917 A | | 10/1996 | Durif et al. |
| 5,574,052 A | | 11/1996 | Rose et al. |
| 5,580,578 A | | 12/1996 | Oshlack et al. |
| 5,580,876 A | | 12/1996 | Crain et al. |
| 5,585,460 A | | 12/1996 | Yamada et al. |
| 5,587,381 A | | 12/1996 | Sinclair |
| 5,601,835 A | | 2/1997 | Sabel et al. |
| 5,604,198 A | | 2/1997 | Poduslo et al. |
| 5,618,553 A | * | 4/1997 | Kelleher .................... 424/428 |
| 5,618,555 A | | 4/1997 | Tokuda et al. |
| 5,629,014 A | * | 5/1997 | Kwiatek et al. ............. 424/449 |
| 5,633,000 A | | 5/1997 | Grossman et al. |
| 5,650,173 A | | 7/1997 | Ramstack et al. |
| 5,651,986 A | | 7/1997 | Brem et al. |
| 5,654,008 A | | 8/1997 | Herbert et al. |
| 5,703,101 A | | 12/1997 | Rose et al. |
| 5,718,921 A | | 2/1998 | Mathiowitz et al. |
| 5,726,190 A | | 3/1998 | Rose et al. |
| 5,732,717 A | * | 3/1998 | Watanabe et al. ........... 128/898 |
| 5,750,136 A | | 5/1998 | Scholz et al. |
| 5,756,483 A | | 5/1998 | Merkus |
| 5,770,231 A | | 6/1998 | Mesens et al. |
| 5,770,606 A | | 6/1998 | El-Rashidy et al. |
| 5,851,547 A | | 12/1998 | Fujioka et al. |
| 5,858,388 A | | 1/1999 | Grossman et al. |
| 5,877,224 A | | 3/1999 | Brocchini et al. |
| 5,919,473 A | * | 7/1999 | Elkhoury .................... 424/422 |
| 5,935,975 A | | 8/1999 | Rose et al. |
| 5,939,094 A | | 8/1999 | Durif et al. |
| 5,965,168 A | | 10/1999 | Mesens et al. |
| 5,968,547 A | | 10/1999 | Reder et al. |
| 5,968,551 A | | 10/1999 | Oshlack et al. |
| 5,980,927 A | | 11/1999 | Nelson et al. |
| 5,980,948 A | | 11/1999 | Goedemoed et al. |
| 5,994,363 A | | 11/1999 | El-Rashidy et al. |
| 6,001,845 A | | 12/1999 | Estok |
| 6,004,962 A | | 12/1999 | Gooberman |
| 6,004,969 A | | 12/1999 | Hu |
| 6,007,841 A | | 12/1999 | Caruso |
| 6,011,043 A | | 1/2000 | Estok |
| 6,117,454 A | | 9/2000 | Kreuter et al. |
| 6,126,956 A | | 10/2000 | Grossman et al. |
| 6,136,818 A | | 10/2000 | Estok |
| 6,203,813 B1 | | 3/2001 | Gooberman |
| 6,228,863 B1 | | 5/2001 | Palermo et al. |
| 6,271,240 B1 | | 8/2001 | Simon |
| 6,342,250 B1 | | 1/2002 | Masters |
| 6,344,212 B2 | | 2/2002 | Reder et al. |
| 6,461,485 B2 | | 10/2002 | Mizouchi et al. |
| 6,495,155 B1 | | 12/2002 | Tice et al. |
| 6,512,009 B1 | | 1/2003 | Daoust et al. |
| 6,541,021 B1 | | 4/2003 | Johnson et al. |
| 6,613,358 B2 | | 9/2003 | Randolph et al. |
| 7,270,830 B2 | | 9/2007 | Reidenberg et al. |
| 2001/0036469 A1 | | 11/2001 | Gooberman |
| 2002/0034534 A1 | | 3/2002 | Barr et al. |
| 2002/0198574 A1 | | 12/2002 | Gumpert |
| 2003/0039689 A1 | | 2/2003 | Chen et al. |
| 2003/0211157 A1 | | 11/2003 | Simon |
| 2004/0009222 A1 | | 1/2004 | Chou et al. |
| 2004/0024006 A1 | | 2/2004 | Simon |
| 2005/0245541 A1 | | 11/2005 | Ehrich et al. |
| 2007/0275031 A1 | | 11/2007 | Patel et al. |
| 2008/0026031 A1 | | 1/2008 | Patel et al. |

FOREIGN PATENT DOCUMENTS

| | | |
|---|---|---|
| EP | 0 226 061 A2 | 6/1987 |
| EP | 0 226 061 A3 | 6/1987 |
| EP | 0 226 061 B1 | 6/1987 |
| EP | 0 478 671 B1 | 4/1992 |
| EP | 0 531 415 B1 | 3/1993 |
| EP | 0 945 133 A1 | 9/1999 |
| JP | 3-193732 A | 8/1991 |
| WO | WO-89/05632 A1 | 6/1989 |
| WO | WO-90/15637 A2 | 12/1990 |
| WO | WO-91/18605 A1 | 12/1991 |
| WO | WO-96/00537 A1 | 1/1996 |
| WO | WO-98/20684 A2 | 5/1998 |
| WO | WO 00/19976 | 4/2000 |
| WO | WO 00/35456 | 6/2000 |
| WO | WO-00/72827 A2 | 12/2000 |
| WO | WO-00/72827 A3 | 12/2000 |
| WO | WO-03/101358 A1 | 12/2003 |
| WO | WO-2004/089375 A1 | 10/2004 |
| WO | WO-2007/139744 A2 | 12/2007 |

OTHER PUBLICATIONS

Patel, R. (2001). "Buprenorphine Implants: Novel Treatment for Opiate Dependence," Poster Presentation: *Pharmaceutical Congress of the Americas*: Orlando, FL, Mar. 24-29, 2001, three pages.

Ciraulo, D.A. et al. (2006). "Pharmacokinetics and Pharmacodynamics of Multiple Sublingual Buprenorphine Tablets in Dose-Escalation Trials," *Pharmacokinetics and Pharmacodynamics* 46:179-192.

Cowan, A. et al. (1977). "The Animal Pharmacology of Buprenorphine, an Oripavine Analgesic Agent," *Br. J. Pharmac.* 60:547-554.

Gueye, P.N. et al. (2001). "Lack of Effect of Single High Doses of Buprenorphine on Arterial Blood Gases in the Rat," *Toxicological Sciences* 62:148-154.

Lesser, G.L. et al. (May/Jun. 1996). "In Vitro and In Vivo Studies of Subcutaneous Hydromorphone Implants Designed for the Treatment of Cancer Pain," *Pain* 65(2,3):265-272.

McAleer, S.D. et al. (Oct. 24, 2003). "Pharmacokinetics of High Dose Buprenorphine Following Single Administration of Sublingual Tablet Formulations in Opiod Naive Healthy Male Volunteers under a Naltrexone Block," *Drug and Alcohol Dependence* 72(1):75-83.

Ohtani, M. et al. (Feb. 1995). "Comparative Analysis of Buprenorphine-and Norbuprenorphine -Induced Analgesic Effects Based on Pharmacokinetic-Pharmacodynamic Modeling," *Journal of Pharmacology and Experimental Therapeutics* 272(2):505-509.

Walsh, S.L. et al. (May 1994). "Clinical Pharmacology of Buprenorphine: Ceiling Effects at High Doses," *Clinical Pharmacology & Therapeutics* 55(5):569-580.

International Search Report mailed on Sep. 18, 2008, for PCT Application No. PCT/US2007/012046, filed on May 18, 2007, eight pages.
Written Opinion mailed Sep. 18, 2008, for PCT Application No. PCT/US2007/012046, filed on May 18, 2007, nine pages.
Anonymous (2005). "The Use of Transdermal Opioids in Patents with Malignant Pain Requires and Individualised and Aggressive Approach," *Drugs Ther. Perspect.* 21(10):24-26.
Anonymous (2007). "Dosing Guidance for Suboxone & Subutex®," located at <http://www.suboxone.com/hcp/opioiddependence/dosing_guide.aspx>, last visited on Jan. 30, 2008, 3 pages.
Anonymous (2007). "Dosing Guidance for Suboxone & Subutex® Maintenance Therapy,", located at <http://www.suboxone.com/hcp/opioiddependence/maintenance_therapy.aspx>, last visited on Jan. 30, 2008, 10 pages.
Anonymous (2007). "Dosing Guidance for Suboxone & Subutex® Short- and Long-term Medical Withdrawal (ie, Detoxification)—Inpatient and Out Patient," located at <http://www.suboxone.com/hcp/opioiddependence/withdrawal.aspx>, last visited on Jan. 30, 2008, 6 pages.
Cowan, A. et al. (1977). "Agonist and Antagonist Properties of Buprenorphine, a New Antinociceptive Agent," *Br. J. Pharmac.* 60:537-545.
Danhof, M. (2007). "Mechanism-based PK-PD Modeling for Prediction Efficacy and Safety," *presented at British Pharmaceutical Conference*, Manchester, England, Sep. 10, 2007, 36 pages.
Elkader, A. et al. (2005). "Buprenorphine: Clinical Pharmacokinetics in the Treatment of Opioid Dependence," *Clin. Pharmacok.* 44(7):661-680.
Kleppner, S.R. et al. (2006). "In-vitro and In-vivo Characterization of a Buprenorphine Delivery System," *J. Pharma. Pharmacol.* 58:295-302.
Kuhlman, J.J. Jr. (1996). "An investigation of Buprenorphine and Norbuprenorphine Plasma Concentrations in Opioid Dependence Therapy: Analysis, Pharmacokinetics and Chronic Administration," A Dissertation submitted to the Faculty of the Graduate School of the University of Maryland in partial fulfillment of the requirements for the degree of Doctor of Philosophy, 140 pages.
Likar, R. (2006). "Transdermal Buprenorphine in the Management of Persistent Pain—Safety Aspects," *Therapeutics and Clinical Risk Management* 2(1):115-125.
Ling, W. et al. (May 1996). "A Controlled Trial Comparing Buprenorphine and Methadone Maintenance in Opioid Dependence," *Arch. Gen. Psychiatry* 53(5):401-407.
Ling, W. (1998). "Buprenorphine Maintenance Treatment of Opiate Dependence: A Multicenter, Randomized Clinical Trial," *Addiction* 93(4):475-486.
Martin, W.R. et al. (1976). "The Effects of Morphine- and Nalorphine- like Drugs in the Nondependent and Morphine-Dependent Chronic Spinal Dog," *J. Pharmacol. Exp. Ther.* 197(3):517-532.
Shippenberg, T.S. et al. (2002). "Recent Advances in Animal Models of Drug Addiction: Definitions and Validation of Animal Models," Chapter 97 *in Neuropsychopharmacology: The Fifth Generation of Progress*, Davis, K.I. et al. eds., Lippincott Williams & Wilkins, Philadelphia, PA, pp. 1381-1397.
Talbot, P.S. et al. (Mar. 2005). "$^{11}$C-GR103545, a Radiotracer for Imaging κ-Opioid Receptors In Vivo with PET: Synthesis and Evaluation in Baboons," *J. Nuc. Med* 46(3):484-494.
Welsh, M.J. et al. (Mar. 1978). "Depression of Ventilation by Dopamine in Man: Evidence for an Effect on the Chemoreceptor Reflex," *J. Clin. Invest.* 61:708-713.
Anonymous (May 14, 2002). "Titan Reports First Quarter 2002 Results," located at <http://www.accessmylibrary.com/coms2/summary_0286-25350537_ITM>, last visited on May 29, 2008, 5 pages.
Anonymous (Jun. 7, 2002). "Titan Announces Probuphine Demonstrates Continuous Delivery of Buprenorphine for Eight Months in Preclinical Studies; Novel Long-Term Delivery System for Treatment of Addiction," located at <http://www.accessmylibrary.com/coms2/summary_0286-25427865_ITM>, last visited on May 29, 2008, 3 pages.
Bullingham, R.E.S. et al. (1981). "Sublingual Buprenorphine Used Postoperatively: Clinical Observations and Preliminary Pharmacokinetic Analysis," *Br. J. Clin. Pharmac.* 12:117-122.

Cassidy, J.P. et al. (1993). "Controlled Buccal Delivery of Buprenorphine," *J. Controlled Release* 25:21-29.
Compton, P. et al. (2006). "Pharmacokinetics, Bioavailability and Opioid Effects of Liquid Versus Tablet Buprenorphine," *Drug and Alcohol Dependence* 82:25-31.
Kuhlman, J.J., Jr. et al. (1998). "Relationship of Plasma Buprenorphine and Norbuprenorphine to Withdrawal Symptoms During Dose Induction, Maintenance and Withdrawal from Sublingual Buprenorphine," *Addiction* 93(4):549-559.
Patel, R.A. (2002). "Long Term Delivery of Buprenorphine by an Implantable Delivery System," *presented at The International Conference on Pain and Chemical Dependency*, New York, NY, Jun. 6-8, 2002, 1 page.
Watanabe, K. (1996). "Rectal Absorption and Mucosal Irritation of Rectal Gels Containing Buprenorphine Hydrochloride Prepared with Water-Soluble Dietary Fibers, Xanthan Gum and Locust Bean Gum," *J. Controlled Release* 38:29-37.
Anonymous (Dec. 14, 2002). "India Infoline Sector Reports Pharmaceuticals," located at <http:www.inidainfoline.com/sect/phfo/ch21.html>, last visited Mar. 27, 2003, 2 pages.
Bibbiani, F. et al. (Date Unknown). "Continuous Apomorphine Administration with Novel EVA Implants Reduces the Risks of Motor Compilations Compared to Pulsatile Apormorphine in L-DOPA-Naïve, MPTP-Lesioned Primates," Abstract Preview: AAN3L_1225, located at <http://www.abstracts-on-line.com>, last visited on Feb. 6, 2003, 1 page.
Chow, B.L.C. et al. (1997). "Effect of Naltrexone and Its Derivatives, Nalmefene and Naltrindole, on Conditioned Anticipatory Behaviour and Saccharin Intake in Rats," *Behavioural Pharmacology* 8(8):725-735.
Croop, R.S. et al. (Dec. 1997). "The Safety Profile of Naltrexone in the Treatment of Alcoholism," *Arch. Gen. Psychiatry* 54:1130-1135.
Dixon, R. et al. (Jan. 1986). "Nalmefene: Intravenous Safety and Kinetics of a New Opioid Antagonist," *Clin. Pharmacol. Ther.* 39(1):49-53.
Dupont (2007). "Elvax® Specialty EVA Resins," located at <http://www2.dupont.com/Elvax/en_US/products/eva_resins.html>, last visited on Nov. 19, 2007, 7 pages.
During, M.J. et al. (Apr. 1989). "Controlled Release of Dopamine from a Polymeric Brain Implant: In Vivo Characterization," *Ann. Neurol.* 25(4):351-356.
European Examination Communication mailed on Aug. 29, 2008, for European Patent Application No. 04753725.3, filed on May 27, 2004, three pages.
Final Office Action mailed on Jul. 22, 2008, for U.S. Appl. No. 10/815,481, filed Mar. 31, 2004, 19 pages.
Freese, A. et al. (1989). "Controlled Release of Dopamine from a Polymeric Brain Implant: In Vitro Characterization," *Exp. Neurol.* 103:234-238.
Fudala, P.J. et al. (Mar. 1991). "Human Pharmacology and Abuse Potential of Nalmefene," *Clin. Pharmacol. Ther.* 49(3):300-306.
Fuller, R.K. et al. (Sep. 19, 1986). "Disulfiram Treatment of Alcoholism: A Veterans Administration Cooperative Study,"*JAMA* 256(11):1449-1455.
Hamilton, R.J. et al. (Jan. 2002). "Complications of Ultrarapid Opioid Detoxification with Subcutaneous Naltrexone Pellets," Acad. Emergency Medicine 9(1):63-68.
Hardman, J.G. et al., eds. (2001). "Dopamine-Receptor Agonists," *in Goodman & Gilman's The Pharmacological Basis of Therapeutics*, Tenth Edition, McGraw-Hill: New York, NY, pp. 557-558.
Hardman, J.G. et al., eds. (2001). "Levodopa," *in Goodman & Gilman's The Pharmacological Basis of Therapeutics*, Tenth Edition, McGraw-Hill: New York, NY, pp. 555-557.
Hubbell, C.L. et al. (1991). "Opioidergic, Serotonergic, and Dopaminergic Manipulations and Rats' Intake of a Sweetened Alcoholic Beverage," *Alcohol* 8:355-367.
International Search Report mailed on Sep. 13, 2004 for PCT Application No. PCT/US2004/010270, filed on Mar. 31, 2004, 5 pages.
International Search Report mailed Dec. 21, 2004 for PCT patent application No. PCT/US2004/016944 filed on May 27, 2004, 6 pages.

Johnsen, J. et al. (1987). "A Double-blind Placebo Controlled Study of Male Alcoholics Given a Subcutaneous Disulfiram Implantation," *British Journal of Addiction* 82(6):607-613.

Johnsen J. et al. (May-Jun. 1991). "Disulfiram Implant: A Double-Blind Placebo Controlled Follow-Up on Treatment Outcome," *Alcohol Clin. and Exp. Res.* 15(3):532-536.

Mason, B.J. et al. (Aug. 1999). "A Double-blind, Placebo-Controlled Study of Oral Nalmefene for Alcohol Dependence," *Arch. Gen. Psychiatry* 56(8):719-724.

Mason, B.J. et al. (Sep./Oct. 1994). "A Double-Blind, Placebo-Controlled Pilot Study to Evaluate the Efficacy and Safety of Oral Nalmefene HCl for Alcohol Dependence," *Alcohol Clin. Exp. Res.* 18(5):1162-1167.

Mehta, M., ed. (1997). *PDR Guide to Drug Interactions Side Effects Indications Contraindications*, 51st edition, Medical Economics Company, Inc.: New Jersey, pp. 957-959 (Interactions Index only).

Michel, M.E. et al. (1985). "Binding of a New Opiate Antagonist, Nalmefene, to Rat Brain Membranes," *Meth. And Find Exptl. Clin Pharmacol.* 7(4):175-177.

Misra, A.L. et al. (1980). "An Improved Long-Acting Delivery System for Narcotic Antagonists," *NIDA Res. Monograph* 28:254-264.

Non-Final Office Action mailed on Nov. 29, 2007, for U.S. Appl. No. 10/815,481, filed Mar. 31, 2004, 8 pages.

O'Malley, S.S. et al. (Mar. 1996). "Six-Month Follow-up of Naltrexone and Psychotherapy for Alcohol Dependence," *Arch. Gen. Psychiatry* 53(3):217-224.

O'Malley, S.S. et al. (Nov. 1992). "Naltrexone and Coping Skills Therapy for Alcohol Dependence: A Controlled Study," *Arch. Gen . Psychiatry* 49(11):881-887.

Oslin, D. et al. (1997). "Naltrexone as an Adjunctive Treatment for Older Patients With Alcohol Dependence," *The American Journal of Geriatric Psychiatry* 5(4):324-332.

Response to Non-Final Office Action submitted to the USPTO on Apr. 28, 2008, for U.S. Appl. No. 10/815,481, filed Mar. 31, 2004, 22 pages.

Sabel, B.A. (1990). "Extended Levodopa Release from Subcutaneously Implanted Polymer Matrix in Rats," *Annals of Neurology* 28(5):714-717.

Schwope, A.D. et al. (1975). "Development of Polyactic/Glycolic Acid Delivery Systems for Use in Treatment of Narcotic Addiction," *NIDA Res. Monograph Series* 4:13-18.

Tabakoff, B. et al. (1983). "Alcohol Interactions with Brain Opiate Recceptors," *Life Sciences* 32:197-204.

Volpicelli, J.R. et al. (Aug. 1997). "Naltrexone and Alcohol Dependence: Role of Subject Compliance," *Arch. Gen. Psychiatry* 54:737-742.

Volpicelli, J.R. et al. (Nov. 1992). "Naltrexone in the Treatment of Alcohol Dependence," *Arch. Gen. Psychiatry* 49:876-880.

Whyte, C.R. et al. (1974). "Disulfiram Implant: A Controlled Trial," *Br. J. Psychiatry* 124:42-44.

Wilson, A. et al. (1976). "Disulfiram Implantation: Placebo, Psychological Deterrent, and Pharmacological Deterrent Effects," *Br. J. Psychiatry* 129:277-280.

Wilson, A. et al. (1978). "Disulfiram Implantation: A Placebo-Controlled Trial with Two-Year Follow-Up," *Journal of Studies on Alcohol* 39(5):809-818.

Evans, H.C. et al. (2003). "Transdermal Buprenorphine," *Drugs* 63(19):1999-2010.

International Search Report mailed on Aug. 20, 2003, for PCT Application No. PCT/US03/17401, 1 page.

Kamei, S. et al. (1996). "Influence of Low-Molecular Weight Fraction of Polymer on Entrapment and Initial Release of Leuprorelin," *Proc. Int. Symp. Control. Rel. Bioact. Mater.* 23:347-348.

McQuinn, R.L. et al. (1995). "Sustained Oral Mucosal Delivery in Human Volunteers of Buprenorphine from a Thin Non-Eroding Mucoadhesive Polymeric Disk," *Journal of Controlled Release* 34:243-250.

Sigmon, S.C. et al. (Nov. 2004). "Evaluation of an Injection Depot Formulation of Burprenorphine: Placebo Comparison," *Addiction* 99(11):1439-1449.

Sigmon, S.C. et al. (2006). "An Injected Depot Formulation of Buprenorphine: Extended Biodelivery and Effects," *Addiction* 101:420-432.

Sobel, B.-F.X. et al. (Jan. 7, 2004). "Open-Label Trial of an Injection Depot Formulation of Buprenorphine in Opioid Detoxification," *Drug and Alcohol Dependence* 73(1):11-22.

Wilding, I.R. et al. (Apr. 30, 1996). "Pharmacokinetic Evaluation of Transdermal Buprenorphine in Man," *International Journal of Therapeutics* 132(1,2):81-87.

Bye, A. et al. (Nov. 2008). "Pharmacokinetic Analyses in Subjects Treated for 6 Months with Buprenorphine Implants," *International Society of Addiction Medicine*, Nov. 16-20, 2008, Cape Town, South Africa, fourteen pages.

Casadonte, P. et al. (Nov. 2008). "Phase 3 Results Evaluating the Safety and Efficacy of a 6-month, Sustained Release, Implantable Formulation of Buprenorphine, (Probuphine®)," *International Society of Addiction Medicine*, Nov. 16-20, 2008, Cape Town, South Africa, twenty-five pages.

Greenwald, M. et al. (2007). "Buprenorphine Duration of Action: $Mu$-opioid Receptor Availability and Pharmacokinetic and Behavioral Indices," *Biol. Psychiatry* 61:101-110.

Malinoff, H.L. et al. (2005). "Sublingual Buprenorphine is Effective in the Treatment of Chronic Pain Syndrome," *American Journal of Therapeutics* 12:379-384.

White, J. et al. (2009). "Open-label Dose-finding Trial of Buprenorphine Implants (Probuphine)® for Treatment of Heroin Dependence," *Drug and Alcohol Dependence* 103:37-43.

Anonymous. (Jul. 2001). "Buprenex®," NDC 12496-0757-1, 2 pages.

Bullingham, R.E.S. et al. (Nov. 1980). "Buprenorphine Kinetics," *Clinical Pharmacology and Therapeutics* 28(5):667-672.

Greenwald, M.K. et al. (2003). "Effects of Buprenorphine Maintenance Dose on µ-Opioid Receptor Availability, Plasma Concentrations, and Antagonist Blockade in Heroin-Dependent Volunteers," *Neuropsychopharmacology* 28:2000-2009.

Johnson, R.E. et al. (May 27, 1992). "A Controlled Trial of Buprenorphine Treatment for Opioid Dependence," *JAMA* 267(20):2750-2755.

June, H.L. et al. (Dec. 1998). "The Opioid Receptor Antagonist Nalmefene Reduces Responding Maintained by Ethanol Presentation: Preclinical Studies in Ethanol-Preferring and Outbred Wistar Rats," *Alcohol Clin. Exp. Res.* 22(9):2174-2185.

Kuhlman, Jr., J.J. et al. (Oct. 1996). "Human Pharmacokinetics of Intravenous, Sublingual, and Buccal Buprenorphine," *Journal of Analytical Toxicology* 20(6):369-378.

(English Translation of the Abstract Only). Lehmann, K.A. (1984). "On-Demand Analgesie: Neue Möglichkeiten zur Behandlung acuter Schmerzen [On Demand Analgesia: New Concepts for Treatment of Acute Pain]," Arzneimittelforschung 34(9A):1108-1114.

Medical Economics—Staff, eds. (2004). "Suboxone® Subutex®," *Physicans' Desk Reference 2004*, 58th Edition, Medical Economic Company, Inc.: Montvale, NJ, Brand and Generic Name Index p. 123, Product Identification Guide p. 333, pp. 2866-2869.

Medical Economics—Staff, eds. (2003). "Buprenex®," *Physicans' Desk Reference 2003*, 57th Edition, Medical Economic Company, Inc.: Montvale, NJ, pp. 2857-2859.

Medical Economics—Staff, eds. (2002). "Buprenex®," *Physicans' Desk Reference 2002*, 56th Edition, Medical Economic Company, Inc.: Montvale, NJ, pp. 2918-2919.

Mendelson, J.H. et al. (Apr. 1989). "Naloxone Suppresses Buprenorphine Stimulation of Plasma Prolactin," *Journal of Clinical Psychopharmacology* 9(2):105-109.

Strain, E.C. et al. (2004). "Relative Bioavailability of Different Buprenorphine Formulations Under Chronic Dosing Conditions," *Drug and Alcohol Dependence* 74:37-43.

Wilson, A. et al (1980). "Disulfiram Implantation: A Trial Using Placebo Implants and Two Types of Controls," *J. Stud. Alcohol* 41(5):429-436.

Yoburn, B.C. et al. (1986). "Pharmacokinetics and Pharmacodynamics of Subcutaneous Naltrexone Pellets in the Rat," *J. Pharmacol. Exp. Ther.* 237(1):126-130.

Kalachandra, S. et al. (2002). "Controlled Drug Release for Oral Condition by a Novel Device Based on Ethylene Vinyl Acetate (EVA)," *Journal of Materials Science: Materials in Medicine* 13:53-58.

Pontani, R.B. et al. (Mar. 1, 1983). "A Long-Acting Buprenorphine Delivery System," *Pharmacology Biochemistry and Behavior* 18(3):471-474.

Supplementary European Search Report mailed on Dec. 1, 2009, for European Patent Application No. 03731501.7, 3 pages.

Lamprecht, A. et al. (2001). "Biodegradable Nanoparticles for Targeted Drug Delivery in Treatment of Inflammatory Bowel Disease," *The Journal of Pharmacology and Experimental Therapeutics* 299(2):775-781.

Zubieta, J-K. et al. (2000). "Buprenorphine-Induced Changes in Mu-opioid Receptor Availability in Male Heroin-Dependent Volunteers: A Preliminary Study," *Neuropsychopharmacology* 23(3):326-334.

Freye, E. et al. (2007). "Opioid Rotation from High-Dose Morphine to Transdermal Buprenorphine (Transtec®) in Chronic Pain Patients," *Pain Practice* 7(2):123-129.

Johnson, R.E. et al. (Mar. 2005). "Buprenorphine: Considerations for Pain Management," *Journal of Pain and Symptom Management* 29(3):297-326.

Kay, D.C. et al. (1981). "Morphine-Like Insomnia from Heroin in Nondependent Human Addicts," *British Journal of Clinical Pharmacology* 11:159-169.

Lester, P.A. et al. (2006). "Comparison of the in vitro Efficacy of $\mu$, $\sigma$, $\kappa$ and $ORL_1$ Receptor Agonists and Non-Selective Opioid Agonists in Dog Brain Membranes," *Brain Research* 1073-1074:290-296.

Nath, R.P. et al. (1999). "Buprenorphine Pharmacokinetics: Relative Bioavailability of Sublingual Tablet and Liquid Formulations," *J. Clin. Pharmacol.* 39:619-623.

Schuh, K.J. et al. (1999). "Pharmacokinetic Comparison of the Buprenorphine Sublingual Liquid and Tablet," *Drug Alcohol Depend.* 56:55-60.

Skingle, M. et al. (1980). "Further Studies on Opiate Receptors That Mediate Antinoception: Tooth Pulp Stimulation in the Dog," *British Journal of Pharmacology*, 70:323-327.

Tigerstedt, I. et al. (1980). "Double-Blind, Multiple-Dose Comparison of Buprenorphine and Morphine in Postoperative Pain," *Acta Anaesthesiologica Scandanavia* 24:462-468.

\* cited by examiner

IMPLANTABLE POLYMERIC DEVICE FOR SUSTAINED RELEASE OF BUPRENORPHINE

CROSS REFERENCE TO RELATED APPLICATIONS

This application claims the benefit of U.S. Provisional Patent Application Ser. No. 60/384,733, filed May 31, 2002, the disclosure of which is incorporated herein by reference in its entirety.

STATEMENT REGARDING FEDERALLY SPONSORED RESEARCH OR DEVELOPMENT

This invention was made in part during work supported by a grant from the National Institute of Mental Health (1R43 MH60037-01). The government has certain rights in the invention.

TECHNICAL FIELD

The invention provides a nonbioerodible, polymeric device for subcutaneous implantation and sustained release of buprenorphine for treatment of opiate addiction or pain.

BACKGROUND OF THE INVENTION

Buprenorphine, a semi-synthetic opiate classified as a "partial agonist" behaves very much like classical mu agonists such as morphine, exerting an analgesic effect through high affinity binding to mu subclass opiate receptors in the central nervous system.

Buprenorphine has been used as an analgesic for treatment of moderate to severe pain in postoperative cancer patients. Therapeutic doses administered by intravenous and intramuscular routes range from 0.3 to 0.6 mg. Buprenorphine produces effects similar to morphine but is 25-40 times more potent and has a large therapeutic index. Buprenorphine stimulates the mu opiate receptors in the brain and produces effects associated with other mu agonists such as morphine. Such effects include analgesia, euphoria, sedation, and respiratory depression. For this reason, oral buprenorphine formulations have the potential for misuse (i.e., diversion for recreational, rather than therapeutic, purposes), making them unsuitable for use as a take-home medication.

Many patients with chronic pain require long-term continuous dosing with opiate analgesics. Effective treatment often necessitates the ingestion of multiple tablets per day. Compliance with this dosing scheme is often poor. Further, enteral drug delivery is poorly tolerated or prohibited in patients with particular indications, such as some patients with cancer-related pain in whom continuous drug delivery is a necessity. However, continuous parenteral delivery of opiate analgesics is expensive, cumbersome, and dependent upon the availability of refrigeration, catheters, pumps, and trained personnel. Further, concerns over drug diversion for illicit use often limits availability of opiate analgesics. An oral tablet containing a combination of buprenorphine and naloxone, an opiate receptor antagonist, has been developed to address this issue (see, e.g., U.S. Pat. No. 4,935,428). If an opiate addict attempts to abuse the combination tablet by dissolving it and injecting it intravenously, unpleasant withdrawal symptoms brought on by the naloxone component will result. However, opiate antagonists such as naloxone may reduce the analgesic effectiveness of buprenorphine to those who are using it therapeutically for pain relief and such antagonists may cause undesirable side effects. Thus, there is a need for an improved buprenorphine formulation which is administrable to those in need of analgesia but which provides a lower potential for abuse.

Buprenorphine has also been studied as a treatment for addiction to heroin and other opiates. Opiate addiction is a major societal problem throughout the world. The general treatment program for such addiction includes incorporation of a drug substitute, e.g., methadone, into an oral formulation for administration to the drug addict. Typically, such drug substitutes function by binding to receptors specific for the drug of abuse. The effectiveness of such treatment depends largely upon adherence to an established treatment schedule. Often, poor compliance with dosing regimens complicates treatment. Further, the cost of such therapy is significant, a large portion of the cost relating to frequent clinic visits and the monitoring of urine tests to assure compliance with drug dosing, as well as pharmacy charges relating to dispensing of methadone. Another problem with oral dosage forms such as powders or tablets is that they can be dissolved in water and concentrated to provide a solution which may be injected by the addict in lieu of the drug of abuse. A means for long-term continuous administration of a drug suitable for treatment of opiate dependency in a form that is not subject to potential abuse, would significantly reduce the compliance problems encountered in drug addiction treatment programs.

Buprenorphine's unique effects and pharmacology make it a clinically attractive treatment option for opiate dependency. For example, buprenorphine produces less euphoria than morphine and heroin. When compared with other opiates, it also causes a significantly lower degree of sedation. Further, direct dependence studies have shown little physical dependence upon withdrawal of the drug.

There is a need for a buprenorphine formulation, suitable for long-term, continuous administration, that will improve compliance for both pain relief and drug dependency treatment regimens. There is also a need for a buprenorphine formulation that will reduce abuse potential, and in which the addition of an antagonist such as naloxone will not be necessary.

BRIEF SUMMARY OF THE INVENTION

The invention provides compositions (i.e., implantable polymeric devices), methods, and kits for treatment of opiate addiction and pain.

In one aspect the invention provides an implantable device for treating opiate addiction, comprising buprenorphine and a biocompatible, nonerodible polymeric matrix, wherein said buprenorphine is encapsulated within said matrix, and wherein when said implantable device is implanted subcutaneously in a mammal, said buprenorphine is continuously released in vivo over a sustained period of time through pores that open to the surface of said matrix at a rate that results in a steady state plasma buprenorphine level of at least about 0.1 ng/ml, typically in the range of about 0.1 to about 70 ng/ml. In some embodiments, the steady state plasma buprenorphine level is about 1 to about 10 ng/ml. In other embodiments, the steady state plasma buprenorphine level is about 1 to about 6 ng/ml. In some embodiments, the polymeric matrix comprises ethylene vinyl acetate copolymer (EVA). In some embodiments wherein the implantable device comprises EVA, the vinyl acetate content is about 33% by weight. The implantable devices generally comprise about 10% to about 85%, often about 50% to about 75% buprenorphine. In one embodiment, the implantable device comprises about 50% buprenorphine. In another embodiment, the implantable device comprises about 75% buprenorphine. In various embodiments, the sustained period of time for buprenorphine release is from about 3 months to about 1 year, or longer, e.g., at least about 3, 6, 9, or 12 months. In some embodiments, the implantable device for treatment of opiate addiction is produced by an extrusion process. In one embodiment, extruded devices comprise dimensions of about 2.4 mm in diameter and about 2.6 cm in length. In other embodiments, extruded devices comprise dimensions of about 2 to about 3 mm in diameter and about 2 to about 3 cm in length. In further embodiments, extruded devices comprises dimensions of about 0.5 to about 7 mm in diameter and about 0.5 to about 10 cm in length. In some embodiments in which extruded devices comprise dimensions of about 2.4 mm in diameter and about 2.6 cm in length, the devices each release about 1 mg buprenorphine per day in vitro.

In another aspect, the invention provides an implantable device for treating pain, comprising buprenorphine and a biocompatible, nonerodible polymeric matrix, wherein said buprenorphine is encapsulated within said matrix, and wherein when said implantable device is subcutaneously implanted in a mammal, said buprenorphine is continuously released in vivo over a sustained period of time through pores that open to the surface of said matrix at a steady state rate of at least about 0.1 mg per day, generally in the range of about 0.1 to about 5 mg per day. In some embodiments, the steady state rate of buprenorphine release is about 0.3 mg per day. In some embodiments, the polymeric matrix comprises EVA. In some embodiments wherein the implantable device comprises EVA, the vinyl acetate content is about 33% by weight. The implantable devices generally comprise about 10% to about 85%, often about 50% to about 75% buprenorphine. In one embodiment, the implantable device comprises about 50% buprenorphine. In another embodiment, the implantable device comprises about 75% buprenorphine and about 25% EVA. In various embodiments, the sustained period of time for buprenorphine release is from about 3 months to about 1 year, or longer, e.g., at least about 3, 6, 9, or 12 months. In some embodiments, the implantable device for treatment of pain is produced by an extrusion process. In one embodiment, extruded devices comprise dimensions of about 2.4 mm in diameter and about 2.6 cm in length. In other embodiments, extruded devices comprise dimensions of about 2 to about 3 mm in diameter and about 2 to about 3 cm in length. In further embodiments, extruded devices comprises dimensions of about 0.5 to about 7 mm in diameter and about 0.5 to about 10 cm in length. In some embodiments in which extruded devices comprise dimensions of about 2.4 mm in diameter and about 2.6 cm in length, the devices each release about 1 mg buprenorphine per day in vitro.

In one aspect, the invention provides a method for treatment of opiate addiction, comprising administering at least one implantable device for treatment of opiate addiction, as described above, subcutaneously, wherein each of said at least one implantable devices comprises buprenorphine encapsulated within a biocompatible, nonerodible polymeric matrix, wherein said buprenorphine is continuously released in vivo over a sustained period of time through pores that open to the surface of said matrix at a rate that results in a steady state plasma buprenorphine level of at least about 0.1 ng/ml, generally about 0.1 to about 70 ng/ml. In some embodiments, the steady state plasma level of buprenorphine is about 1 to about 10 ng/ml. In other embodiments, the steady state plasma level of buprenorphine is about 1 to about 6 ng/ml. In one embodiment, the method includes a multiplicity of individual implantable devices, wherein the combination of the implantable devices continuously releases buprenorphine in vivo over a sustained period of time at a steady state rate that results in a plasma buprenorphine level of about 0.1 to about 70, about 1 to about 10, or about 1 to about 6 ng/ml. In some embodiments, the polymeric matrix comprises EVA. In one embodiment, implantable devices comprise about 75% buprenorphine and about 25% EVA. In another embodiment, implantable devices comprise about 50% buprenorphine. In some embodiments wherein implantable devices comprise EVA, the vinyl acetate content is about 33% by weight. In various embodiments, the sustained period of time for buprenorphine release is from about 3 months to about 1 year, or longer, e.g., at least about 3, 6, 9, or 12 months. In some embodiments, implantable devices for treatment of opiate addiction are produced by an extrusion process. In one embodiment, extruded devices comprise dimensions of about 2.4 mm in diameter and about 2.6 cm in length. In other embodiments, extruded devices comprises dimensions of about 2 to about 3 mm in diameter and about 2 to about 3 cm in length. In further embodiments, extruded devices comprise dimensions of about 0.5 to about 7 mm in diameter and about 0.5 to about 10 cm in length. In some embodiments in which extruded devices comprises dimensions of about 2.4 mm in diameter and about 2.6 cm in length, the devices each release about 1 mg buprenorphine per day in vitro. In methods of the invention, the implantable devices are administered by subcutaneous implantation. In various embodiments, the devices are subcutaneously implanted at a site selected from the group consisting of the upper arm, the back, and the abdomen.

In another aspect, the invention provides a method for treatment of pain, comprising administering at least one implantable device for treatment of pain, as described above, subcutaneously, wherein each of said at least one implantable devices comprises buprenorphine encapsulated within a biocompatible, nonerodible polymeric matrix, wherein said buprenorphine is continuously released in vivo over a sustained period of time through pores that open to the surface of said matrix at a steady state rate of at least about 0.1 mg per day, often in the range of about 0.1 to about 5 or about 0.2 to about 1 mg per day. In some embodiments, the steady state rate of buprenorphine release is about 0.3 mg per day. In one embodiment, the method includes a multiplicity of individual implantable devices, wherein the combination of the implantable devices continuously releases buprenorphine in vivo over a sustained period of time at a steady state rate of about 0.1 to about 5, about 0.2 to about 1, or about 0.3 mg per day. In some embodiments, the polymeric matrix comprises EVA. In one embodiment, implantable devices comprise about 75% buprenorphine and about 25% EVA. In another embodiment, implantable devices comprise about 50% buprenorphine. In some embodiments wherein implantable devices comprise EVA, the vinyl acetate content is about 33% by weight. In various embodiments, the sustained period of time for buprenorphine release is from about 3 months to about 1 year, or longer, e.g., at least about 3, 6, 9, or 12 months. In some embodiments, implantable devices for treatment of pain are produced by an extrusion process. In methods of the invention, the implantable devices are administered by subcutaneous implantation. In various embodiments, the devices are subcutaneously implanted at a site selected from the group consisting of the upper arm, the back, and the abdomen.

In one aspect, the invention provides a kit for use in treatment of opiate addiction, comprising at least one implantable device for treatment of opiate addiction, as described above, comprising buprenorphine encapsulated within a biocompatible, nonerodible polymeric matrix, wherein when said at least one implantable device is implanted subcutaneously in a mammal, said buprenorphine is continuously released in vivo over a sustained period of time through pores that open to the surface of said matrix at a rate that results in a steady state plasma level of about 0.1 to about 70 ng/ml, and instructions for use. In some embodiments, the steady state plasma level is about 1 to about 10 ng/ml. In other embodiments, the steady state plasma level is about 1 to about 6 ng/ml. In some embodiments, kits include a multiplicity of individual implantable devices, wherein when said multiplicity of devices is implanted subcutaneously in a mammal, the combination of the implantable devices continuously releases buprenorphine in vivo over a sustained period of time at a rate that results in a steady state plasma level of about 0.1 to about 70, often about 1 to about 10, more often about 1 to about 6 ng/ml. In one embodiment, each of the individual implantable devices releases buprenorphine at a rate of about 1 mg per day in vitro. In some embodiments, the polymeric matrix comprises EVA. In various embodiments, implantable devices comprise about 10 to about 85% buprenorphine. In some embodiments wherein implantable devices comprise EVA, the vinyl acetate content is about 33% by weight.

In another aspect, the invention provides a kit for use in treatment of pain, comprising at least one implantable device for treatment of pain, as described above, comprising buprenorphine encapsulated within a biocompatible, nonerodible polymeric matrix, wherein when said at least one implantable device is implanted subcutaneously in a mammal, said buprenorphine is continuously released in vivo over a sustained period of time through pores that open to the surface at a steady state rate of at least about 0.1 mg per day, generally in the range of about 0.1 to about 5 or about 0.2 to about 1 mg per day, and instructions for use. In one embodiment, the steady state rate of buprenorphine release is about 0.3 mg per day. In some embodiments, kits include a multiplicity of individual implantable devices, wherein when said multiplicity of devices is implanted subcutaneously in a mammal, the combination of the implantable devices continuously releases buprenorphine in vivo over a sustained period of time at a rate of about 0.1 to about 5, 0.2 to about 1, or about 0.3 mg per day. In some embodiments, the polymeric matrix comprises EVA. In various embodiments, implantable devices comprise about 10 to about 85% buprenorphine. In some embodiments wherein implantable devices comprise EVA, the vinyl acetate content is about 33% by weight.

BRIEF DESCRIPTION OF THE DRAWINGS

FIG. 1A shows the average cumulative release of buprenorphine HCl in 0.5% SDS at 37° C. FIG. 1B shows the average daily release of buprenorphine HCl in 0.5% SDS at 37° C.

DETAILED DESCRIPTION OF THE INVENTION

The invention provides a biocompatible, nonerodible polymeric device, which permits controlled, sustained release of buprenorphine over extended periods of time when implanted subcutaneously in an individual in need of treatment.

Continuous release of a compound in vivo over an extended duration may be achieved via implantation of a device containing the compound encapsulated in a nonerodible polymeric matrix. Examples of implantable, nonerodible polymeric devices for continuous drug release are described in, e.g., U.S. Pat. Nos. 4,883,666, 5,114,719, and 5,601,835. Implantable devices improve compliance with drug dosing regimens, due to continuous release of the drug from the polymeric matrix, and reduce abuse potential since such devices are not as subject to diversion as other formulations, such as, for example, oral dosage forms.

Implantation of the device and extended release of buprenorphine limits or prevents diversion of the drug to nonintended users and improves compliance with dosing regimens, eliminating the need for repeated injections or ingestion of pills or tablets. An implantable, sustained-release device according to the present invention also permits achievement of more constant blood levels of buprenorphine than injectable or oral dosage forms, thereby minimizing side effects.

Previous vehicles for long term delivery of buprenorphine have included biodegradable polymers (U.S. Pat. No. 5,486,362). However, in contrast to the present invention, such polymers do not release compounds at linear rates for extended time periods of several months or longer, because channels form in the matrix as it erodes, resulting in increased release rates over time. The present invention includes a biocompatible, nonerodible polymer that exhibits generally linear release kinetics for buprenorphine in vivo, after an initial burst.

Implantable Polymeric Devices for Treatment of Opiate Addiction or Pain

The invention includes implantable devices for treatment of opiate addiction or pain, including buprenorphine encapsulated in a polymeric, nonerodible matrix. As used herein, "buprenorphine" refers to buprenorphine free base and pharmaceutically acceptable salts thereof, such as buprenorphine HCl, and norbuprenorphine. Incorporation of buprenorphine into the polymeric matrix causes the formation of a series of interconnecting channels and pores that are accessible to the surface for release of the drug. Where appropriate, a coating that is impermeable to the drug is placed over at least a portion of the device to further regulate the rate of release. When implanted subcutaneously, devices of the invention continuously release buprenorphine for an extended period of time with a pseudo or near zero order release rate. After an initial burst following implantation, release rates are typically within about 10-20% of the steady state average. In some embodiments, the initial burst of buprenorphine released in vivo after implantation is reduced or minimized by prewashing the implantable devices before implantation to remove surface buprenorphine. Prewashing may be performed in any solution in which buprenorphine is soluble, for example 30 minutes in ethanol or normal saline.

As used herein, "nonerodible matrix" refers to a polymeric carrier that is sufficiently resistant to chemical and/or physical destruction by the environment of use such that the matrix remains essentially intact throughout the release period. The polymer is generally hydrophobic so that it retains its integrity for a suitable period of time when placed in an aqueous environment, such as the body of a mammal, and stable enough to be stored for an extended period before use. The ideal polymer must also be strong, yet flexible enough so that it does not crumble or fragment during use. Nonerodible matrices remain intact in vivo for extended periods of time, typically months or years. Drug molecules encapsulated in the matrix are released over time via diffusion through channels and pores in a sustained and predictable manner. The release rate can be altered by modifying the percent drug loading, porosity of the matrix, structure of the implantable device, or hydrophobicity of the matrix, or by adding a hydrophobic coating to the exterior of the implantable device.

Typically, ethylene vinyl acetate copolymer (EVA) is used as the polymeric matrix, but other nonerodible materials may be used. Examples of other suitable materials include silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyurethane, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, and chlorosulphonated polyolefines, and combinations thereof.

Implantable devices of the invention are typically formulated with buprenorphine loading of about 10% to about 85%. Often, the devices include about 50% to about 75% buprenorphine. Devices are sometimes formulated as compositions including about 75% buprenorphine and about 25% EVA (33% vinyl acetate). In various embodiments, devices include any of at least about 10, 20, 30, 40, 50, 55, 60, 65, 70, 75, 80, or 85% buprenorphine. Devices may be produced using an extrusion process, wherein ground EVA is blended with buprenorphine, melted, and extruded into rod-shaped structures. Rods are cut into individual implantable devices of the desired length, packaged, and sterilized prior to use. Other methods for encapsulating therapeutic compounds in implantable polymeric, nonerodible matrices are well known to those of skill in the art. Such methods include, for example, solvent casting (see, e.g., U.S. Pat. Nos. 4,883,666, 5,114, 719, and 5,601,835). A skilled artisan would be able to readily determine an appropriate method of preparing such an implantable device, depending on the shape, size, drug loading, and release kinetics desired for a particular type of patient or clinical indication.

Devices of the invention are suitable for sustained release of buprenorphine for treatment of opiate addiction or pain. As used herein, "sustained release" refers to the release of buprenorphine such that the blood concentration remains within the therapeutic range but below toxic levels for an extended duration. Devices of the invention generally exhibit near zero-order pharmacokinetics in vivo, similar to kinetics achieved with an IV drip, but without the need for external medical equipment and personnel associated with intravenous methods. Generally, after implantation, the devices release therapeutically effective amounts of buprenorphine for periods of several months up to one year or longer. Often, the duration of implantation, with continuous release of buprenorphine, is from about 3 months to about 2 years, about 3 months to about 1 year, about 3 months to about 9 months, or about 3 months to about 6 months. In various embodiments, therapeutically effective amounts of buprenorphine are released for at least about 3, 6, 9, 12, 15, 18, 21, or 24 months.

Multiple implantable devices may be used, or the size and shape of the devices may be modified, to achieve a desired overall dosage; Implantable devices are often about 0.5 to about 10, more often about 1.5 to about 5, most often about 2 to about 3 cm in length, and are often about 0.5 to about 7, more often about 1.5 to about 5, most often about 2 to about 3 mm in diameter. The release rate of implantable devices may also be modified by changing the vinyl acetate content in the EVA polymer matrix. The vinyl acetate content is often about 2 to about 40, more often about 10 to about 35, most often about 30 to about 35% by weight.

The desired dosage rate will depend upon factors such as the underlying condition for which buprenorphine is being administered, and the physiology of a particular patient, but will be readily ascertainable to physicians. For treatment of opiate addiction, buprenorphine is desirably released at a rate that maintains plasma levels of the drug at a therapeutically effective level. Often, a desirable plasma level of buprenorphine for treatment of opiate addiction is in the range of about 0.1 to about 70 ng/ml, more often about 1 to about 10 ng/ml, most often about 1 to about 6 ng/ml. In various embodiments for treatment of opiate addiction, buprenorphine is released from one or more devices in vivo at a rate that results in a plasma level of at least about 0.1, 0.5, 1, 2, 3, 4, 5, 6, 8, 10, 15, 25, 50, or 70 ng/ml. For treatment of pain, a therapeutically effective amount of buprenorphine is typically about 0.1 to about 5 mg/day, sometimes about 0.2 to about 1 mg/day, often about 0.3 mg/day, but may be modified depending upon the nature of the pain condition being treated and the particular patient involved. In various embodiments for treatment of pain, one or more devices are used that are capable of releasing at least about 0.1, 0.2, 0.3, 0.4, 0.5, 1, 2, 3, 4, or 5 mg/day in vivo or in vitro. As used herein, "therapeutically effective amount" or "therapeutically effective level" refers to the amount of buprenorphine that will render a desired therapeutic outcome (i.e., reduction of self-administration of nonprescribed drugs, or analgesic relief of pain).

Methods of the Invention

The invention provides methods for treatment of opiate addiction and pain. Methods of the invention include subcutaneous administration of one or more polymeric implantable devices which include buprenorphine encapsulated within a biocompatible, nonerodible polymeric matrix such as EVA, and release of buprenorphine in a controlled manner over an extended period of time through multiple pores that open to the surface of the implantable device(s). Often, implantable devices are produced via an extrusion process, as described above.

Implantable devices are administered by subcutaneous implantation to an individual in need of treatment. As used herein, "individual" refers to a mammal, typically a human in need of treatment for opiate addiction or pain. Generally, implantable devices are administered by subcutaneous implantation at sites on the upper arm, back, or abdomen of an individual. Other suitable sites for administration may be readily determined by a medical professional. Multiple implantable devices may be administered to achieve a desired dosage for treatment.

Typically, in a method for treatment of opiate addiction, an implantable device or devices are administered that will release buprenorphine at a rate that will maintain a therapeutically effective plasma level for an extended period of time of at least about 3 months. When multiple devices are administered, the combination of the devices releases buprenorphine at a rate that will achieve a therapeutically effective plasma level. A therapeutically effective plasma level for treatment of opiate addiction is often about 0.1 to about 70 ng/ml, more often about 1 to about 10 ng/ml, most often about 1 to about 6 ng/ml. Often, sustained release at this dosage rate occurs for about 3 months to about 1 year or longer (e.g., at least about 3, 6, 9, or 12 months). As used herein, "opiate addiction" or "opiate dependency" refers to dependence by an individual on an opiate substance which is treatable by administration of a substitute substance, such as methadone or buprenorphine. It is anticipated that the implantable devices of the invention will alleviate compliance and diversion problems encountered with traditional methadone treatment regimens, as described above.

Further, in accordance with the present invention, a method of alleviating pain is provided which includes subcutaneous administration of an implantable nonerodible polymeric device which releases an analgesically effective amount of buprenorphine in a controlled manner for an extended period of time, i.e. about 3 months to about 1 year (e.g., at least about 3, 6, 9, or 12 months) or longer, to an individual exhibiting pain. An implantable device is chosen for a particular patient or pain indication such that an analgesically effective amount of buprenorphine will be continuously released. As used herein, the term "analgesically effective amount" refers to an amount of buprenorphine sufficient to achieve a reduction in or elimination of pain in a mammalian subject without loss of consciousness. The effectiveness of analgesia provided by an analgesic substance can be assessed by methods that are well known to those skilled in the art. For example, U.S. Pat. No. 6,228,863 describes assessment by direct measurement in human patients or by the use of one or more surrogate measures. Direct measurement may include scoring an analgesic questionnaire reported by patients at serial times following administration of the analgesic substance. Summary measures of analgesia include the sum of pain intensity difference (SPID) and total pain relief (TOTPAR). Surrogate measures for determining analgesic effectiveness in human subjects include assessment of sedation, respiratory rate and/or pupil size, and visual analogue scale for drug effect. Effectiveness of analgesia may also be assessed using animal models. For example, U.S. Pat. No. 4,599,342 describes a mouse hot plate test and a phenylquinone writhing test model for assessing the extent of analgesia.

The method of alleviating pain according to the present invention is applicable to the treatment of all pain conditions which require continuous administration of an analgesic substance, e.g., postoperative pain, cancer pain, arthritic pain, lumbosacral pain, musculoskeletal pain, neuropathic pain, etc. This list, however, should not be interpreted as exhaustive. It is contemplated that the method of the invention will improve compliance with dosing regimens for therapeutic pain relief, while reducing the amount of opiate substances that are available for diversion to nonintended users, i.e., drug addicts. Long term continuous release should also reduce or eliminate the peaks and troughs of blood analgesic concentration associated with other formulations such as oral dosage forms. Typically, the steady state release rate of buprenorphine used for pain relief methods is from about 0.1 to about 5, sometimes about 0.2 to about 1, often about 0.3 mg per day.

In any of the above methods, the length of time during which buprenorphine is continuously administered may be extended by reimplanting additional implantable devices in an individual receiving treatment before or after plasma levels of buprenorphine begin to decline, to maintain buprenorphine at the desired steady state level.

Kits

The invention also provides kits for use in treatment of opiate addiction or pain. The kits include at least one implantable, nonerodible device of the type herein described, capable of delivering long-term therapeutic levels of buprenorphine, in suitable packaging, along with instructions providing information to the user and/or health care provider regarding subcutaneous implantation and use of the system for treating drug dependence or pain. Kits may also include literature discussing performance of the implantable devices of the invention. Kits include a delivery system, i.e., one or a multiplicity of implantable devices, capable of providing sustained release of therapeutic levels of buprenorphine for at least about 3 months. Kits for treatment of opiate addiction typically contain a polymeric, nonerodible delivery system capable of continuously releasing buprenorphine at a rate sufficient to achieve a therapeutically effective plasma level of about 0.1 to about 70, about 1 to about 10, or about 1 to about 6 ng/ml for at least about 3 months. Kits for treatment of pain typically contain a delivery system capable of releasing a total continuous analgesically effective dosage of about 0.1 to about 5, about 0.2 to about 1, or about 0.3 mg buprenorphine per day for at least about 3 months. In kits of the invention, implantable devices may be preloaded into devices such as, for example, syringes or trocars, capable of administering them by subcutaneous implantation into patients.

EXAMPLES

The following examples are intended to illustrate but not limit the invention.

Example 1

Materials and Methods

Materials

The following materials were used:
Buprenorphine HCl, 99.3%, supplied by Macfarlan Smith Limited, Wheatfield Road, Edinburgh, EH 11 2QA
Buprenorphine base, supplied by Diosynth B. V. Vlijtseweg 130, 7317 AK Apeldoorn, The Netherlands
Buprenorphine HCl, supplied by Diosynth B. V. Vlijtseweg 130, 7317 AK Apeldoorn, The Netherlands
Methanol-ChromAR, HPLC grade, supplied by Mallinckrodt, St. Louis, Mo.
Acetonitrile, HPLC grade, supplied by Mallinckrodt, St. Louis, Mo.
Sodium lauryl sulfate, 99%, supplied by Sigma Chemicals, St. Louis, Mo.
EVA, 33% vinyl acetate, supplied by Equistar Chemicals, LP, Houston, Tex.
Tower Plasti-Peel pouches, Catalog #30307PN, supplied by DRG Medical Packaging, Mundelein, Ill.

Preparation of Implantable Devices

Buprenorphine is available as a salt (HCl) and as a free base. The implantable device is intended to release drug over a 3-month period or longer, so preliminary studies were performed to select the form of buprenorphine suitable for sustained release. Buprenorphine was incorporated at 50% drug load in the copolymer, using the free base form and the HCl salt. Extruded rods were prepared and comparative in vitro evaluations were conducted to select the drug form, based on the results of these studies.

Implantable devices were prepared using an extrusion process. As a result of initial loading experiments with lactose, two sets of extrusion parameters were identified that produced implantable devices with a smooth exterior finish and homogeneous drug content. The extrusion parameters were as follows:

| Set 1 | |
|---|---|
| Zone 1: | 210° F. |
| Zone 2: | 230° F. |
| Zone 3: | 210° F. |
| Die: | 214° F. |
| RPM: | 67 |
| Die orifice: | 2.18 mm |

Set 1 parameters were used for the preparation of rods incorporating 50% buprenorphine free base and HCl salt.

| Set 2 | |
|---|---|
| Zone 1: | 210° F. |
| Zone 2: | 230° F. |
| Zone 3: | 230° F. |
| Die: | 240° F. |
| RPM: | 40 |
| Die orifice: | 1.95 mm |

Set 2 parameters were used for the preparation of rods incorporating 75% buprenorphine HCl salt, which were used for in vitro and in vivo studies as described below.

The ground copolymer and compound to be incorporated were used as received from the manufacturer. The extruded rods were cut into uniform lengths of 25 mm, packaged in polyester/Tyvek bags, heat sealed, and shipped to Steris/Isomedix (Libertyville, Ill.) for terminal sterilization by gamma irradiation.

HPLC Assays

HPLC analysis, was used to determine the rate of in vitro release of buprenorphine from buprenorphine-containing implants. Chromatography was performed using a Waters Novapak C-18 (150 mm×3.9 mm, SN. E5003B) column and 0.05 M sodium acetate, pH 5 (Solution A) and a mixture of methanol/acetonitrile (2:1 v/v) (Solution B) as the mobile phase, at a ratio of 35% A and 65% B and a flow rate of 1 ml/min. The injection volume was 100 µl. Detection was accomplished by means of a UV/VIS (Waters Model 490) detector at a wavelength of 285 nm. Instrument control and data acquisitions were facilitated using a Waters Millennium (V 2.15) software package. The external calibration was obtained using buprenorphine standard solutions prepared in 2:1 (v/v) acetonitrile:methanol.

The calibration curve for the buprenorphine standard over a concentration range of 2.5-500 µg/ml indicated linearity, with r2 values greater than 0.99.

LC/MS/MS Assay

An LC/MS/MS method was used to determine levels of buprenorphine released from the implants in vivo.

Buprenorphine

Dog plasma (0.500 ml) containing buprenorphine and a D4-buprenorphine internal standard was extracted with hexane/isoamyl alcohol. Following centrifugation, transfer of the organic layer and evaporation, the dried extract was derivatized with pentafluoropropionic anhydride (PFPA). After the reaction, the excess reagent was evaporated and an aliquot of the reconstituted extract was injected onto a SCIEX API III Plus LC-MS-MS apparatus in positive ion mode equipped with an HPLC column. Peak areas of the m/z 596 to 564 product ion of buprenorphine-PFP were measured against the m/z 600 to 568 product ion of the internal standard in MRM mode. Quantitation was performed using a weighted linear least squares regression analysis generated from spiked plasma calibration samples.

Norbuprenorphine

Dog plasma (0.500 ml) containing norbuprenorphine and a D3-norbuprenorphine internal standard was basified and extracted with ethyl acetate. Following evaporation, the dried extract was derivatized with acetic anhydride. After the reaction, the excess reagent was evaporated and an aliquot of the reconstituted extract was injected onto a SCIEX API III-Plus LC-MS-MS apparatus equipped with an HPLC column. Peak areas of the m/z 586 to 498 product ion of the norbuprenorphine derivative was measured against the peak areas of the m/z 589 to 501 product ion of the internal standard. Quantitation was performed using the peak areas of the m/z 589 to 501 product ion of the internal standard. Quantitation was performed using a weighted linear least squares regression analysis generated from fortified plasma calibration samples.

Example 2

In Vitro Characterization of Extruded Implantable Devices

Extruded rods prepared as described above were characterized for total drug load and for rate of drug release.

Assessment of Drug Loading

Extruded rods were accurately weighed, placed in tightly closed borosilicate glass jars containing 50 ml of methanol, and continuously stirred at room temperature. Sample aliquots were removed periodically and analyzed by HPLC. Initial experiments indicated that the incorporated compounds were completely extracted within 24 hr. Irradiated and nonirradiated rods were compared side by side.

Drug loading studies indicated that the physical mixtures were homogeneous and contained the estimated quantities of buprenorphine. Table 1 shows the recovery for the free base (FB) and HCl salt at 50% loading. Table 2 shows the recovery of buprenorphine HCl at 75% loading, and indicates that the average drug load before and after gamma radiation was >75%.

TABLE 1

Recovery of buprenorphine at 50% drug loading.

| Drug | Sample 1 (% drug load) | Sample 2 (% drug load) | Average (% drug load) |
|---|---|---|---|
| Buprenorphine HCl | 51.0 | 49.6 | 50.3 |
| Buprenorphine FB | 45.5 | 46.5 | 46.0 |

TABLE 2

Recovery of buprenorphine HCl at 75% drug loading.

| Before Radiation (% drug load) | After Radiation (% drug load) |
|---|---|
| Average = 77.3 SD = +/−4.2 | Average = 75.5 SD = +/−3.6 |

Assessment of Drug Release

Experiments were performed to determine the rate of buprenorphine released from the extruded rods. The medium for these studies was 0.5% sodium lauryl (dodecyl) sulfate (SDS). The preweighed rods were placed in 100 ml screw cap Ears containing 50 ml of medium and placed on an orbital shaker. The orbital shaker was housed in an incubator maintained at 37° C. Sampling of the medium was performed by replacing the media periodically. The samples obtained were analyzed by HPLC.

Figure 1:
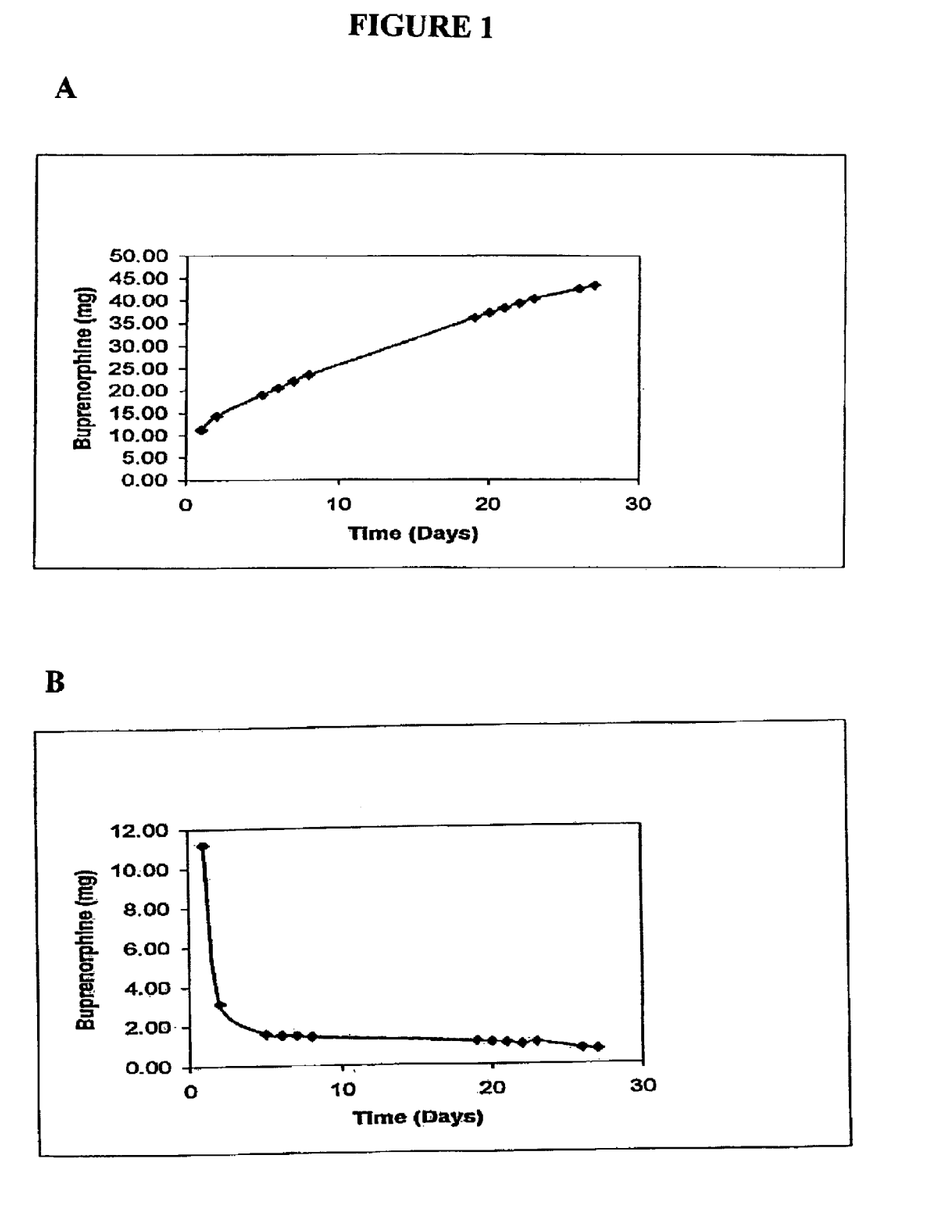
FIG. 1 depicts in vitro release of buprenorphine over time from a single irradiated extruded rod containing 75% buprenorphine HCl and 25% EVA (33% vinyl acetate).

Comparison of the in vitro release of buprenorphine base and salt form indicated that daily release for the HCl salt, after an initial burst, was closer than that of the free base to the desired range of about 1 mg/day (FIG. 1). Thus, the HCl salt was selected for further studies.

Example 3

In Vivo Evaluation of Drug Loaded Implantable Devices

Three female beagle dogs were administered two sterilized implantable devices each containing 75% buprenorphine HCl in EVA containing 33% vinyl acetate, as described above (2 mm diameter×2.6 cm length rods). Implantable devices were administered by subcutaneous injection to the dorsal region of each dog using a trocar. Blood samples were withdrawn periodically over a period of 84 days and frozen. The frozen samples were analyzed by LC/MS/MS for content of buprenorphine and norbuprenorphine (the major metabolite).

Figure 2:
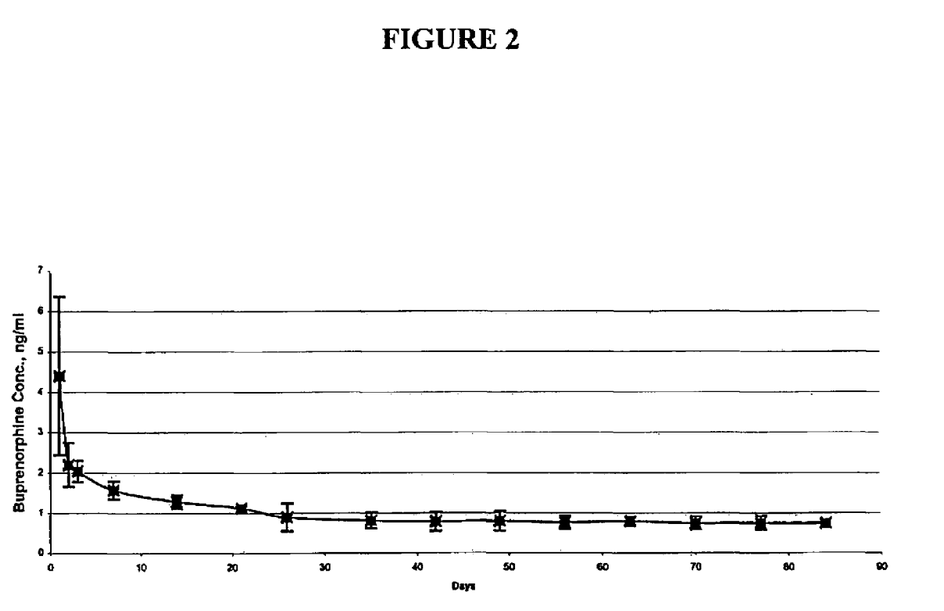
FIG. 2 depicts in vivo release of buprenorphine from devices of the invention implanted subcutaneously in dogs for 84 days. Two devices, each with dimensions of about 2.6 cm in length and about 2 mm in diameter, and containing 75% buprenorphine HCl and 25% EVA (33% vinyl acetate), were implanted in each dog.

After an initial burst, the mean buprenorphine plasma levels were maintained around 0.75-1.0 ng/ml through day 84. The mean buprenorphine and norbuprenorphine levels were similar in all three dogs. The peak concentration of buprenorphine in the plasma ranged from 2.41 to 6.32 ng/ml. After the initial burst effect, a slow decrease in plasma concentration of buprenorphine was observed for all the dogs. On day 84, plasma concentration of buprenorphine ranged from 0.72 to 0.99 ng/ml. No signs of toxicity or irritation and/or inflammation at the sites of implantation were observed in any of the dogs. Further, no vascularization or minimal fibrous capsule formation were observed. The plasma concentration of buprenorphine over time for this experiment is shown in FIG. 2.

Example 4

Long Term Delivery of Burenorphine via an Implantable Delivery System in vivo

In vivo release of buprenorphine from polymeric implantable devices was investigated in toxicology studies in beagle dogs over an eight month period of time. Four dosage groups were treated with 2, 8, 16, or 24 implantable devices (rod-shaped devices containing 25% buprenorphine HCl and 75% EVA with 33% vinyl acetate, as described in Example 3). Implantable devices were administered subcutaneously in the dorsal regions of dogs via trocar under sterile conditions. Blood samples were collected from the jugular veins at various times for 8 months post implantation. Plasma concentrations of buprenorphine were quantified by LC/MS/MS. Animals were monitored for complications including irritation, inflammation, or infection at the treatment site. Pharmacokinetic parameters observed for the different dosage groups are represented in Table 3.

TABLE 3

Pharmacokinetic Parameters Calculated from Plasma Concentrations

| Number of Implants | Mean $C_{max}^a$ (ng/mL) | Mean $t_{max}^b$ (day) | Mean $C_{ss}^c$ (ng/mL) | Half-Life to $C_{ss}$ (weeks) | Number of Dogs, n |
|---|---|---|---|---|---|
| 2 | 4.4 | 1 | 0.81 + 0.1 | 0.7 | 3 |
| 8 | 21.6 | 1 | 3.2 + 0.4 | 2 | 2 |
| 16 | 36.1 | 1 | 4.6 + 0.5 | 2 | 2 |
| 24 | 74.6 | 1 | 9.3 + 0.7 | 2 | 10 |

Figure 3:
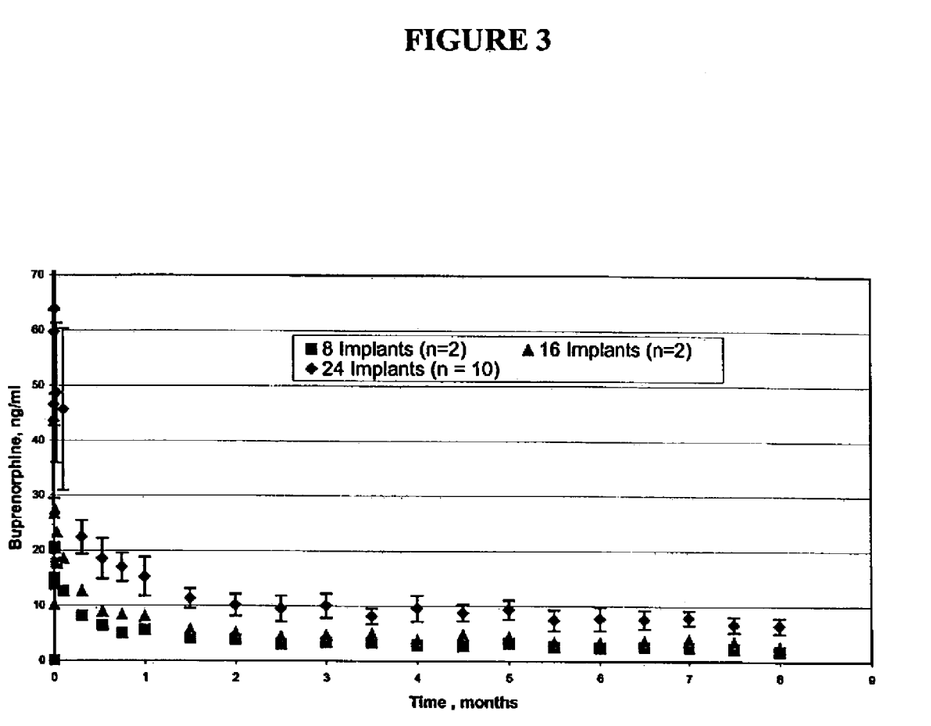
FIG. 3 depicts in vivo release of buprenorphine when 8, 16, or 24 implantable devices were implanted subcutaneously in dogs for 8 months.
Figure 4:
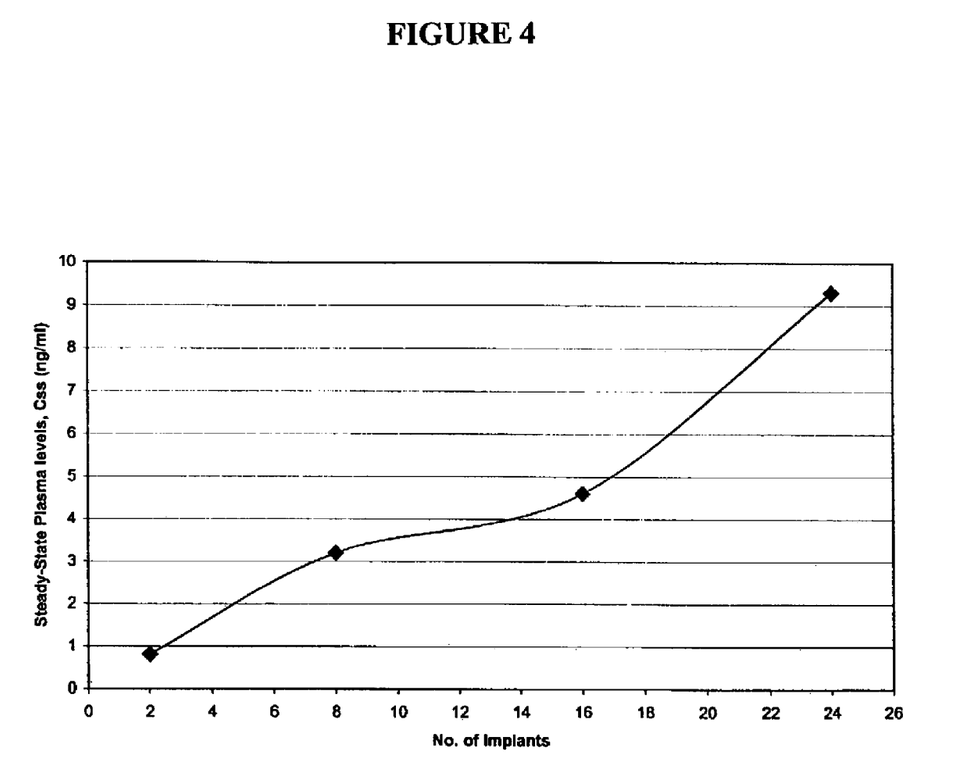
FIG. 4 depicts the steady state plasma concentration of buprenorphine achieved when 2, 8, 16, or 24 implantable devices were implanted subcutaneously in dogs.

$^a$Maximum concentration of buprenorphine achieved in plasma
$^b$Time of maximum plasma concentration of buprenorphine
$^c$Mean steady-state plasma concentration After an initial burst, pharmacokinetics were linear and dose proportional with 2 and 8 implantable devices, and were saturable and nonlinear with 16 and 24 devices (FIG. 3). Steady-state concentrations of 0.81±0.1 and 3.2±0.4 ng/ml were achieved within 3 weeks with 2 and 8 devices, respectively (FIG. 4). Steady-state concentrations of 4.6±0.5 and 9.3±0.7 ng/ml were achieved within 8 weeks with 16 devices and 10 weeks with 24 devices, respectively. Upon reaching steady state, buprenorphine levels remained steady, with a concentration variability of about 10-20%, until 8 months post implantation, at which time the implantable devices were removed. Norbuprenorphine plasma concentrations remained below detectable levels. The additional time required to reach steady state with 16-24 implantable devices may be attributable to limited diffusion of the drug due to saturation of the space between the devices and blood capillaries, or due to saturation of capillary absorptive surface area.

No significant systemic or local (implantation site) adverse effects were observed in any of the dogs. Minor irritation at the treatment site was observed in three dogs. No adverse behavioral effects were observed other than lethargy on the first day after implantation for animals receiving the maximum dosage (i.e., 24 devices). Upon removal of the devices after 8 months, no areas of necrosis or visible vascularization were observed in the tissue that had been surrounding the devices.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entirety

We claim:

1. A method for treating opiate addiction in a human in need thereof, comprising subcutaneously implanting at least one implantable device comprising buprenorphine and ethylene vinyl acetate copolymer (EVA), wherein said device comprises a polymeric matrix comprising buprenorphine blended with said EVA copolymer, wherein said buprenorphine is continuously released in vivo over a sustained period of time through pores that open to the surface of said matrix at a rate that results in a steady state plasma buprenorphine level for at least about 3 months, wherein said device does not comprise a coating that is impermeable to buprenorphine, wherein said device does not comprise external medical equipment, and wherein said at least one device releases buprenorphine at a rate that results in a therapeutically effective steady state plasma level of about 0.1 ng/ml to about 1 ng/ml to a human in need of treatment for opiate addiction.

2. A method according to claim 1, wherein said EVA comprises about 33% vinyl acetate.

3. A method according to claim 2, wherein said implantable device comprises about 10% to about 85% buprenorphine.

4. A method according to claim 3, wherein said implantable device comprises about 50% buprenorphine.

5. A method according to claim 3, wherein said implantable device comprises about 75% buprenorphine.

6. A method according to claim 2, wherein the implantable device is produced by an extrusion process.

7. A method according to claim 6, wherein the implantable device comprises dimensions of about 1.5 to about 5 mm in diameter and about 0.5 to about 7 cm in length.

8. The method of claim 1, wherein said device is washed with ethanol prior to subcutaneous implantation.

9. The method of claim 8, wherein said washing with ethanol removes surface buprenorphine and reduces the initial burst of buprenorphine released in vivo after subcutaneous implantation relative to an unwashed device.

* * * * *